United States Patent [19]

Nachman

[11] 4,244,373
[45] Jan. 13, 1981

[54] ELECTRICAL STIMULATION DENTAL DEVICE

[76] Inventor: Marvin J. Nachman, 315 Saybrook Rd., Villanova, Pa. 19085

[21] Appl. No.: 906,446

[22] Filed: May 17, 1978

[51] Int. Cl.³ .............................................. A61N 1/04
[52] U.S. Cl. ................................. 128/419 F; 128/787
[58] Field of Search .............. 128/82.1, 419 F, 419 R, 128/801; 32/14 B

[56] References Cited

U.S. PATENT DOCUMENTS

| | | | |
|---|---|---|---|
| 285,977 | 10/1883 | Dennis | 128/787 |
| 3,207,161 | 9/1965 | Dietz | 128/787 |
| 3,234,942 | 2/1966 | Simor | 128/172.1 |
| 3,401,690 | 9/1968 | Martin | 128/172.1 |
| 3,842,841 | 10/1974 | Brigaton et al. | 128/419 F |
| 4,153,060 | 5/1979 | Korostoff | 128/787 |

*Primary Examiner*—William E. Kamm
*Attorney, Agent, or Firm*—Paul Maleson

[57] ABSTRACT

An electrical stimulating dental device for electrically stimulating the periodontium bone region within the mouth of a patient. The dental device includes a power supply system for producing an electrical current. The power supply system may provide for a DC current or in one of the embodiments provide for a pulse electromagnetic wave generation. A first electrode defining a cathode element is electrically coupled to the power supply system and in one form of the device interfaces with the surface of the gingivae lining within the mouth of the patient. A second electrode element is electrically coupled to the power supply system and may be coupled to a remote portion of the body of the patient. In another form of the invention, first and second cathode electrode elements are interfaced with opposing transverse sides of the gingivae lining for passage of the current therethrough. Anode electrode elements may be placed in interfacing contact with the lip, cheek or palate of the user. By passage of an electrical current of a predetermined value the dental device stimulates osteogenesis in the neighborhood of the cathode element.

9 Claims, 12 Drawing Figures

ELECTRICAL STIMULATION DENTAL DEVICE

BACKGROUND OF THE INVENTION

1. Field of the Invention

This invention is directed to dental devices. In particular, this invention is directed to dental devices for electrically stimulating the periodontium region within the mouth of the patient. More in particular, this invention is directed to a dental device for providing an electrical current of a predetermined value to the alveolar bone region. Still further, this invention is directed to an electrically stimulating dental device which interfaces with the gingivae lining within the oral cavity of a user. More in particular, this invention pertains to an electrically stimulating dental device which provides for subcutaneous insert into the alveolar bone region within the oral cavity. Additionally, this invention relates to an electrically stimulating dental device which is clamped on opposing sides of the gingivae lining in a particular region of the oral cavity for producing an electrical current therethrough.

2. Prior Art

Medical devices for providing electrical stimulation to stimulate osteogenesis are known in the art. However, in some prior systems, such devices are applicable to portions of the body remote from the oral cavity. Specifically, some of such prior art devices are applied to limb areas for stimulation of osteogenesis.

Other prior art medical devices do not provide for appropriate clamping mechanisms of the device in order that such may be mounted within the oral cavity of a patient. Such prior art medical devices relate to systems which are generally massive in nature and cannot be inserted into the oral cavity for promotion of tissue regeneration or osteogenesis.

In other prior art systems, the power system is large in nature and is essentially not applicable for insertion into the oral cavity of a patient.

To the knowledge of applicant, there has been no practical and useful application of electrical stimuli to the human body for soft tissue regeneration as opposed to electrical stimuli to osseous material.

DESCRIPTION OF THE PREFERRED EMBODIMENTS

Figure 1:
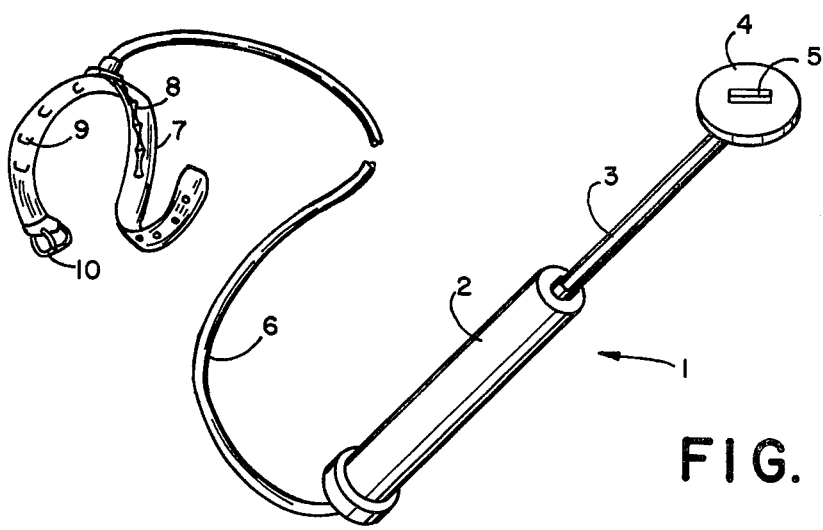
FIG. 1 is a perspective view of the dental device showing the embodiment where the dental device is a surface applicator.

Referring now to FIGS. 1-10 there is shown a plurality of dental devices 1, 11, 20, 26, 28 and 39 all operable under the same inventive concept, which are utilized for electrically stimulating the periodontium region within the mouth of a patient. In a number of prior medical studies, electrical stimulation has been found to induce osteogenesis and to possibly provide increased healing rates for gingiva infections.

A plurality of investigations previously performed has provided the general result that low current electrical stimulation to bone area regions stimulate osteogenesis in the neighborhood of cathode or the negative electrode elements. Numerous parametric studies directed to electrical stimulation in bone area regions has provided a number of theories on why osteogensis has been induced. However, it is not believed that the total mechanism of artificial electrical stimulation of osteogenesis is fully understood at the present time.

Through various laboratory studies it has been found that when low voltage DC currents are applied, electrolysis, where hydrogen is produced at the cathode has not been found to take place. In such studies, it has been found that oxygen is generally consumed at the cathode and hydroxyl radicals are generated. There seems to be a general boundary line of 1.0 volt or less which produces the hydroxyl radical generation. As voltage values rise, the oxygen consumption becomes less and electrolysis apparently is induced, responsively leading to a generation of hydrogen at the cathode.

When a sufficiently low voltage is applied, there is a related oxygen consumption and a responsive production of hydrogen. Oxygen consumption provides for a decreasing oxygen tension in the local tissue surrounding the electrically stimulated area.

In various studies it has been shown that where there is a low oxygen tension in surrounding tissue, bone formation has been found to be maximized due to a low partial oxygen pressure found at the bone cartilage junction. It is further noted that it has been shown that there is an increased bone growth rate found to occur in various low oxygen environments and further that bone cells follow a predominantly anaerobic metabolic pathway.

Further, at various low voltages, hydroxyl radicals have also been found to be produced in the area of electrical stimulation, tissue environment has been found to become more alkaline. Alkaline environments are generally favorable to calcification due to the fact that there has been found high pH values in the zone of hypertrophic cells in various experiments performed.

There are a number of other parameters associated with osteogenesis which are not fully understood due to the fact that magnetically induced currents have also been found to aid in such a process. Initial experiments tend to imply that alternating current and current produced by means of utilizing dissimilar metals may also cause osteogenesis. However, it is evident that in such cases there is no cathode inserted into any tissue area and this leads prior investigators to note that there are probably no oxygen lowering effects as is provided when a DC current is applied.

The dental device of the subject inventive concept has also been found to aid in reducing gingivae infections. These invections have been reduced and eliminated subsequent to the application of cathodic electrical stimuli. Subsequent to the application of the electrical stimuli to diseased periodontal tissue, utilizing the devices of the subject inventive concept, the gingivae was found to have stopped bleeding which has been a characteristic parameter of diseased periodontal tissue.

It is believed that possibly the application of electrical stimuli actuates a morphogenetic switch type mechanism. This may act as a primary cellular messenger causing polarization of the multiplicity of cell ions. This polarization may activate the production of cyclic adenosine 3', 5' monophosphate, commonly referred to as the secondary cellular messenger (cyclic AMP).

Cyclic AMP is an enzyme which serves as the stimulus for the production of other enzymatic reactions which are generally charactertistic of the ribonucleas chain of the cell being stimulated. Prior to any newly created cells being formed, a blastema is formed in the neighborhood of a diseased tissue and mitotic activity then provides for cellular regeneration. This finally results in the regeneration of new cells. Apparently this operates on the diseased tissue of the gingivae in the manner of a purging stimulus which possibly causes the influx or generation of additional antibodies in the neighborhood of the infection. Alternately, or in combination, the effect on the diseased tissue may be the increase in the circulation and the fluid level of the infected cells which may then cause absorbtion and elimination of the infected tissue cells.

Referring now to FIG. 1 there is shown surface applicator 1 for electrically stimulating the periodontium region within the mouth of a patient. In practice, applicator 1 is provided for contiguous placement in the gingivae area in order that first electrode 5 contacts the gingivae lining within the mouth of the patient. Handle 2 is generally cylindrical in nature and adapted for being held with one hand of the user. Handle 2 in this embodiment contains the power supply system for producing the electrical current. Handle 2 is coupled to platform 4 by extended arm 3. Extended arm 3 may be tubular in contour and contain a lead for coupling the power supply within handle 2 to the first electrode 5.

Surface applicator 1 terminates in disc member 4 having a recessed section wherein first electrode 5 extends to an upper surface thereof for providing contact with the gingivae lining of the patient being treated. Where a DC current is being applied, first electrode 5 is the cathodic element in surface applicator 1.

Handle 2 is coupled to strap member 7 through coupling tube 6. Coupling tube 6 has a through opening within which an extended lead passes from the power supply system within handle 2 to the anode 8. Strap 7 is adapted for removeable securement to the arm or other limb of the patient through strap buckle 10. In this manner, the second electrode or anode element 8 is electrically coupled to the power supply system within handle 2 at a remote portion of the body of the patient when taken with respect to the affected area in the gingivae. Anode 8 mounted on the strap 7 includes an extension lug of electrically conductive metal 9 to provide contact with the epidermis of the patient in the arm area.

It is to be understood that in general, the external anode contact 9 requires the use of an electrolyte in order to reduce skin resistance. Output of current from the power supply within handle 2 will be generally in the range of 6.0–20.0 microamperes applied to the gingivae when a stainless steel material is used as the cathodic electrode. In some cases due to the mucous lining resistance factor of the mouth, the output current may have to be increased substantially, possibly into the 100.0 microampere range. However, when other electrode materials are used such as platinum, palladium, or silver, lower currents, possibly in the nanoampere range may be as effective.

It has been found that when a DC current is induced in the motor nerves for muscles, a shock occurs and the muscle contracts. This complex reaction is believed to act as a stimulus for any cellular activity for the growth and repair of damaged cells generally in the area of the cathode. It is believed that this principle is applicable to the generation of osteogenesis and chondrogenesis in periodontium areas within the mouth of the patient when the current is brought into the direct contact with the gingivae lining.

Figure 2:
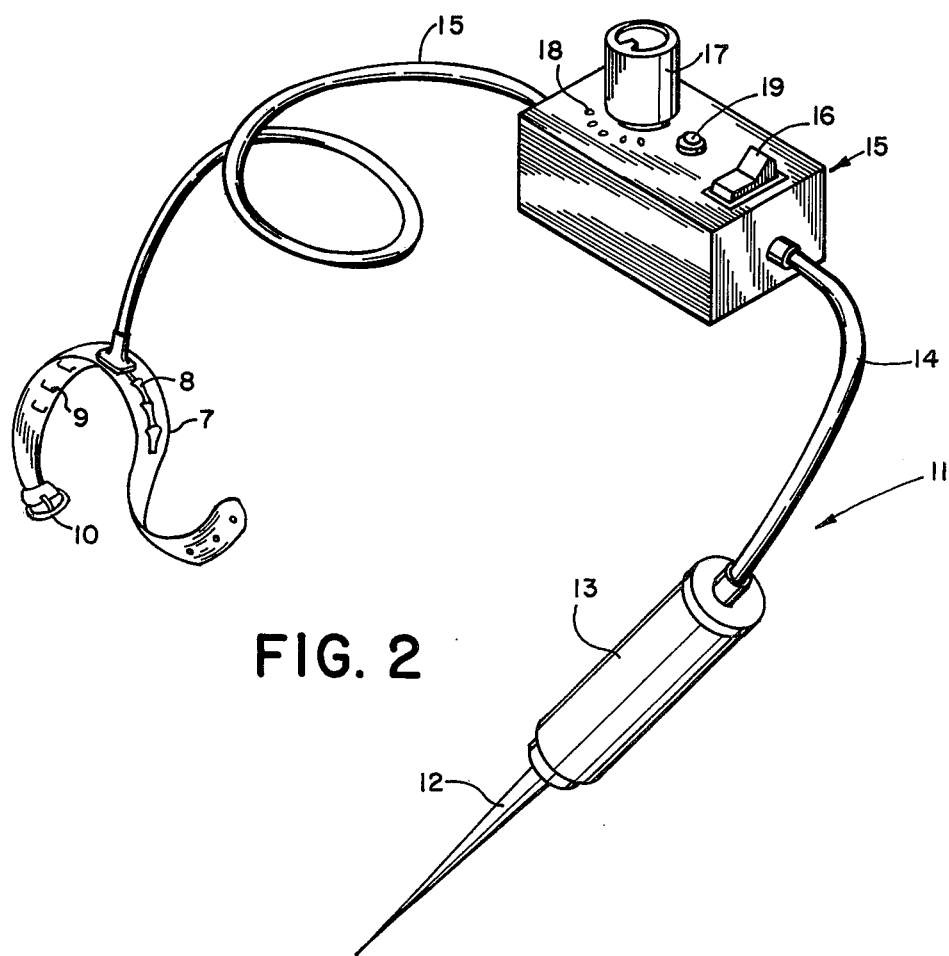
FIG. 2 is a perspective view of the electrically stimulating dental device showing an embodiment wherein the applicator is applicable for subcutaneous use.

Referring now to FIG. 2 there is shown a second embodiment of the dental device describing subctaneous applicator 11. Subcutaneous applicator 11 is specifically adapted for insert into the gingivae lining in the neighborhood of the alveolar bone region to be affected by the electrical stimulation. Subcutaneous applicator 11 includes gingivae lining insert element or needle 12 for entry through the gingivae lining internal thereto. It is to be noted that generally only the top of needle 12 is non-insulated when maximum electrical stimulation of the alveolar region is desired. In this embodiment, needle 12 is coupled to a standard lead internal to needle 12 and passing to power supply 15. For convenience in manual manipulation, handle 13 is provided.

Power supply 15, containing the power supply system to be described in later paragraphs includes a standard on/off switch 16 a potentiometer dial 17 having a scale 18 for varying the magnitude of the current being applied through gingivae lining insert element 12. Additionally, an indicating light such as an LED element 19 may be incorporated into power supply box 15 in order to give indication of whether the power supply is on or in an off mode condition.

On an opposing side of power supply 15, coupling 14' passes from power supply 15 and provides a current lead for anode element 8 and associated anode contact element 9. As in the case in the first embodiment provided and described in previous paragraphs, anode element 8 is strapped to a limb of the user through strap 7 and is removeably secureable thereto through buckle 10. Coupling tube 14 passing from power supply 15 provides a housing sheet for a lead from power supply 15 to needle 12 which defines the cathodic element in the system.

Figure 3:
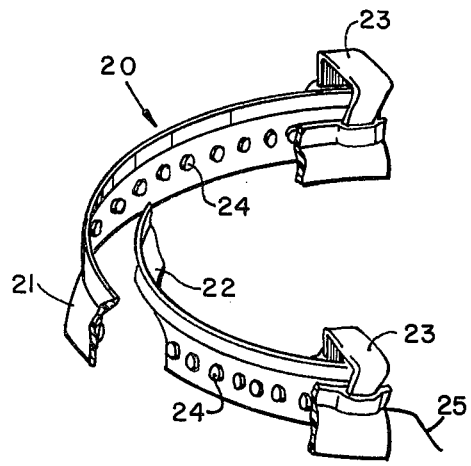
FIG. 3 is a perspective view of an embodiment of the dental device applicable for clamping within the oral cavity on opposing sides of the gingiva lining of a patient.

Referring now to FIG. 3 there is shown another embodiment of the overall dental device for applying electrical stimuli to the periodontium area. In this embodiment, first clamping dental device 20 is mounted on opposing transverse sides of the gingivae lining as is seen, is arcuate in contour passing in a coincident direction defined by a contour of the gingivae lining of the patient. First clamping dental device 20 is formed of first frame wall 22 and second frame wall 21 passing in substantially parallel contours in an arcuate manner.

In general, first frame wall and second frame wall 21 may be formed of plastic material or some like composition generally inert to the internal chemical compositions found in oral cavities of human beings.

First frame wall 22 and second frame wall 21 are displaced each from the other in the transverse direction and are mounted on opposing sides of the gingivae lining through a pair of spring clips 23 which are secured respectively to second frame wall 21 and first frame wall 22. Clips 23 are biased in an inward direction and compressively hold the gingivae of the patient therebetween to maintain contact of second frame wall 21 and first frame wall 22 with opposing transverse sides of the gingivae lining.

As can be seen from FIG. 3, electrodes 24 are formed and embedded within first frame wall 22 and second frame 21 form the cathodic elements for passage of current through the periodontium. Electrodes 24 are discrete cathode elemental segments mounted on the arcuate contour of both first and second frame walls 22 and 21. Additionally, each of the discrete electrode elements 24 are electrically coupled each to the other in series alignment by the lead wires extending from conductor 25. Although not shown, the anode portion of the conductor 25 is in contact with a skin surface in order to complete the electrical circuit.

Thus, in the embodiment shown in FIG. 3, it is clearly seen that first frame wall 22 and second frame wall 21 are spaced apart each from the other joined through clip 23 for resiliently securing second frame wall and first frame wall 21 and 22 for gripping contact of the gingivae lining of the patient. Further, clips 23 which join first and second frame walls 22 and 21 include a U-shaped spring element contour biased in a direction generally forcing first and second frame walls 22 and 21 toward each other. With this type of connecting capability, first clamping dental device 20 is adapted for compressive insert around the gingivae lining of the patient.

Figure 4:
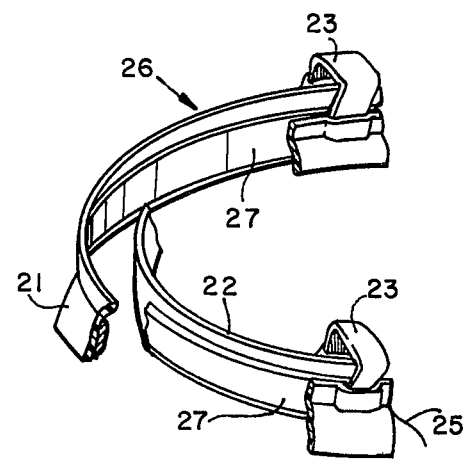
FIG. 4 is a perspective view partially cut away of an embodiment of the dental device wherein the electrodes are strip electrodes.

Still another embodiment, as provided in FIG. 4, shows second clamping dental device 26 having essentially second frame wall 21 and first frame wall 22 in a similar arcuate contour as that provided for first clamping dental device 20. The joining of second frame wall 21 and first frame wall 22 in this embodiment is provided by spring clips 23 similar in nature to those previously described for the embodiment shown in FIG. 3.

The basic variation of the embodiment of second clamped dental device 26 is that cathode electrode elements 27 are not discrete elements in nature but consist of electrode strips 27. Electrode strips 27 are formed of an electrically conducting metal which is generally inert to enzymes and other chemical compositions found in the oral cavity of a patient. Electrode strips 27 as was the case of electrodes 24 in the previous embodiment are electrically coupled to conductor 25 passing to a power supply system for generation of the electrical stimuli. A second lead from the power supply system is coupled to a suitable anodic electrode in contact with a skin surface of the body of the user.

As is evident, in both embodiments of FIG. 3 and FIG. 4, electrodes 24 or 27 formed on one of the frame walls 21 and 22 is connected to the one terminal of the power supply system and an anodic electrode in contact with a skin surface is coupled to the second terminal of the power supply system as was seen in the prior embodiments previously described.

Figure 5:
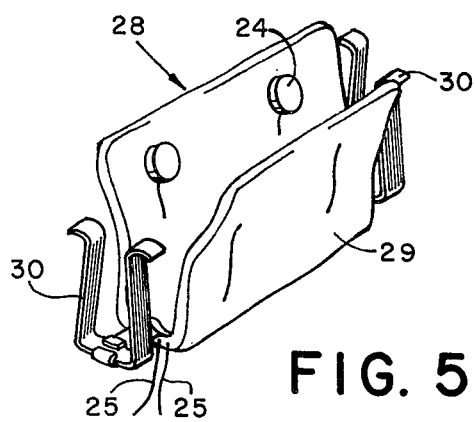
FIG. 5 is an embodiment of the dental device showing a linearly directed applicator having discrete electrode elements mounted thereon.
Figure 7:
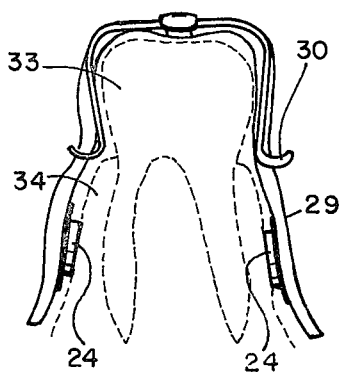
FIG. 7 is an end view of the embodiment shown in FIG. 5 with the gingiva lining with a tooth shown in phantom line drawings.

Referring now to FIGS. 5 and 7 there is shown linearly clamped dental device 28. As is seen in these embodiments, first and second frame walls of the system are formed in one piece contour through main structure 29 which may be composed of a plastic material. In this embodiment, opposing frame walls are joined each to the other in a generally U-shaped structure. As can be seen in FIG. 5, electrodes 24 extend from a surface of structure 29 and contact the gingivae lining on opposing transverse sides thereof as is shown in FIG. 7.

In this embodiment, a pair of clips 30 are mounted on opposing longitudinal ends of main structure 29 and are joined each to the other through a metal bar or some like element mounted within the base of main structure 29. Clips 30 are generally U-shaped in contour and are biased in a direction towards each other in order that they fittingly engage opposing transverse sides of gingivae lining of the patient.

Electrodes 24 on both opposing sides of main structure 29 are coupled respectively to one terminal of the power supply system. An anode element in contact with a skin surface is coupled to the second terminal of the power supply system, as was the case in the embodiments previously referred to.

Figure 6:
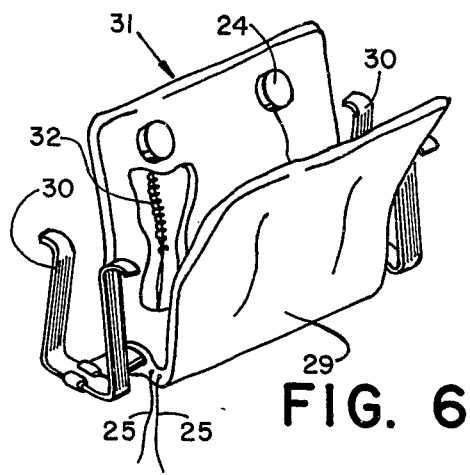
FIG. 6 is an embodiment of the dental device providing for a pulsed electromagnetic radiation within the body of the dental device.

FIG. 6 is a directed to an electromagnetic wave generation system and includes coils 32 in combination with pole pieces 24 formed in main structure 29. Electromagnetic clamp dental device 31 is coupled to an electromagnetic generation system through conductor leads 25 and is mounted to the opposing gingivea lining sections to be treated through the standard spring clips 30 as has previously been discussed. It is to be understood that magnetic contact points 24 will be formed of an electromagnetic material, such as ferrite ceramics, or other suitable non-toxic materials.

Figure 8:
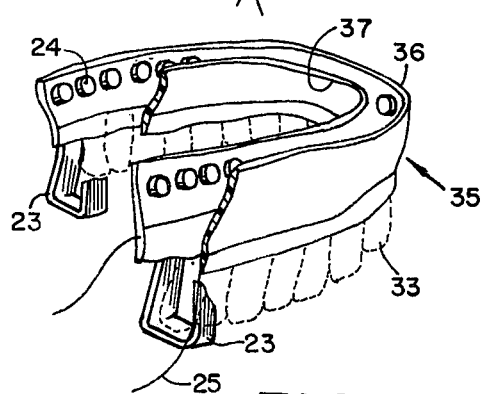
FIG. 8 is another embodiment of a clamping of the dental device provided for an arcuate contour.

Referring now to FIG. 8, there is shown molded dental device 35. As seen, dental device 35 is adapted to be inserted into the oral cavity for mating interface throughout a portion segment or substantially all of the upper mouth region. Obviously, it is to be understood molded dental device 35 may be formed for interfacing relationship with the lower mouth region. Spring clip members 23, either passing under teeth 33, or mounted to the rear of teeth 33, maintain first and second wall members 36 and 37 in a biased condition.

First wall member 36 includes cathodic electrodes 24 coupled to leads 25. Similarly, cathodic 24 coupled to leads 25 are mounted to second wall member 37. Cathode electrodes 24 are forced into contact with opposing sides of the gingivae lining and are operationally activated similar to the embodiment shown in FIG. 3. An anode electrode in contact with the skin surface as previously described is coupled to another terminal of the power supply system.

Figure 9:
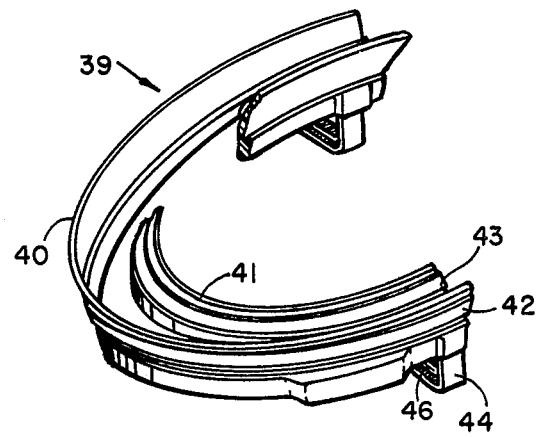
FIG. 9 is an embodiment of the dental device having a power generating system incorporated therein.
Figure 10:
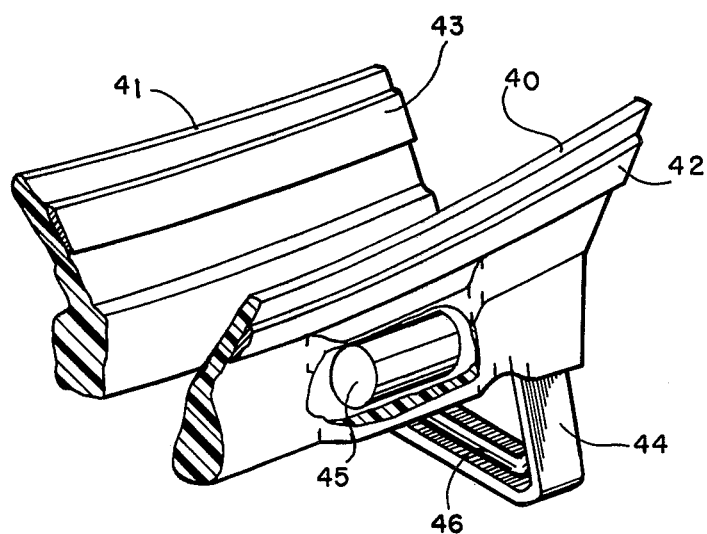
FIG. 10 is an exploded view partially cut away of the dental device as shown in FIG. 9.

Referring now to FIGS. 9 and 10 there is shown power supply incorporated clamping device 39. In this embodiment, first and second frame wall members are joined each to the other through resilient securing mechanism 44 defining spring clips of a nature similar to those previously discussed. Spring clips 44 cause biasing of the first and second wall members 41 and 40 towards each other against opposing sides of the gingivae lining. Incorporated within second wall 40 is a power supply 45 which generates the appropriate current to the effected area.

In this embodiment, it is clearly seen that cathodic electrodes 43 are mounted on walls 40 and 41 for contact interface with the gingivae lining. Additionally, anodic electrode 42 is secured to an outer wall of second wall member 40 to bear against the inner wall of the lip of the user.

Figure 11:
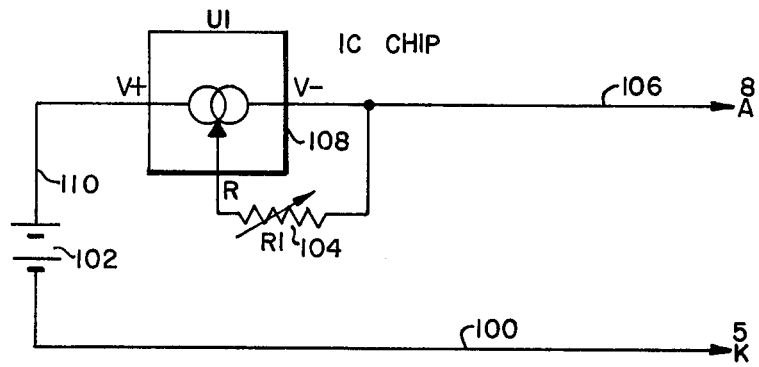
FIG. 11 is a schematic electrical drawing showing an electrical circuit for producing a predetermined current value; and, FIG. 12 is an electrical schematic diagram showing a pulsed electromagnetic circuit for producing an electromagnetic wave generation.

Referring now to FIG. 11 there is shown a schematic diagram for one of a number of electrical circuits which may be used to produce a constant DC current. In general battery 102 may be a General Electric battery model No. S312T2 or equivalent silver oxide cell having a value of 1.5 volts or multiples thereof dependent upon the utilization thereof. Current flows from battery 102 through lead 110 into integrated chip 108 which may be a National Semiconductor chip model No. LM234H. IC chip 108 is an adjustable current source and for the purposes of the subject invention the current is regulated to approximately 20.0 microamperes as defined and regulated by resistance element 104 which may be a potentiometer such as that provided by element 17 shown in FIG. 2. Current passes from IC chip 108 to anode 8 along output line 106. As is evident, current then passes from the anode 8 through the tissue to cathode 5 returning to battery 102 through line 100.

Figure 12:
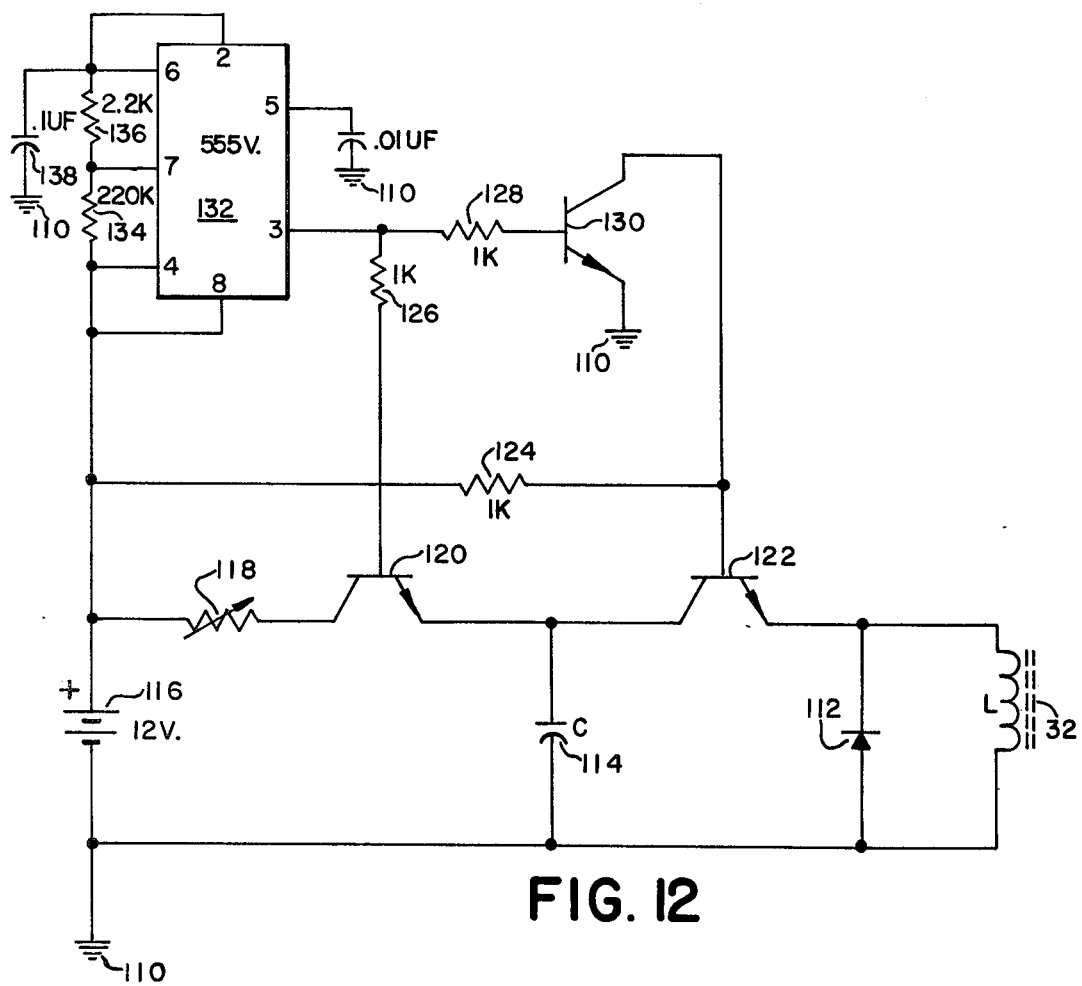

Referring now to FIG. 12 there is shown the electrical schematic diagram directed to a pulsed electromagnetic circuit for periodontium stimulators as may be applied to the embodiment as shown in FIG. 6. Integrated circuit oscillator 132 coupled to resistors 134 and 136 as well as capacitor 138 generates an essentially non-symmetrical square wave form approximating 12.0 volts initiating from battery 116. Transistor 120 is essentially a switching element and is forced into conduction responsive to the output of oscillator 32. Capacitor 114 charges through transistor 120 and current limiting resistor 118 from battery 116. Resistor 118 may be a potentiometer which can then be used to adjust the intensity of the magnetic field produced.

When the output of oscillator 132 drops to ground potential 110, transistor 120 is turned into an off condition and responsively transistor 122 is turned on through the inverting transistor 130.

Capacitor 114 will subsequently discharge through transistor 122 and coil 32 in order to generate a magnetic field. Oscillator 132 subsequently returns to a positive output responsive to the particular time constants associated with the circuit. Transistor 122 is then turned to an off condition and coil 32 discharges through the diode 112. Discharge of inductance through diode 112 is a rapid transient condition and produces a short magnetic pulse in an opposite direction from that originally produced by the capacitor 114 discharge to coil 32. This results in magnetic field pulses at a rate determined by oscillator 132 considerations.

What is claimed is:

1. A dental device for electrically stimulating a periodontium region within the mouth of a patient comprising:
   (a) power supply means for producing a direct electrical current in the approximate range of 6–20 microamperes;
   (b) an electrode housing releaseably securable to opposing transverse sides of an external surface of the gingivae lining within the mouth of said patient,
   (c) first cathodic electrode means being electrically coupled to said power supply means and adapted to directly contact the gingivae lining within said mouth of said patient; and,
   (d) second anodic electrode means being mounted on said electrode housing and electrically coupled to said power supply means, said second electrode means adapted to directly contact the inner wall of said mouth of said patient.

2. A dental device for electrically stimulating a periodontium region within the mouth of a patient comprising:
   (a) power supply means for producing a direct electrical current in the approximate range of 6–20 microamperes;
   (b) frame means releaseably securable to opposing transverse sides of an external surface of the gingivae lining within said mouth of said patient;
   (c) first cathodic electrode means being electrically coupled to said power supply means and adapted to directly contact said external surface of said gingivae lining, said first electrode means for contiguous interface with opposing external transverse sides of said gingivae lining, said first electrode means being secured to said frame means and extending therefrom for contact with said external surface of said gingivae lining, and,
   (d) second anodic electrode means being secured to said frame means and adapted to directly contact said patient other than at said periodontium region and electrically coupled to said power supply means.

3. The dental device as recited in claim 2 where said frame means includes:
   (a) a first frame wall extending in a direction defined by a contour of said gingivae lining, said first electrode means secured to said first frame wall; and,
   (b) a second frame wall extending in said contour direction of said gingivae lining, said first electrode means being additionally secured to said second frame wall.

4. The dental device as recited in claim 3 where said first frame wall is resiliently secured to said second frame wall for gripping contact of said gingivae lining between said first and second frame walls.

5. The dental devices as recited in claim 4 including clip means mounted to said first and second frame walls, said clip means extending in a transverse direction with respect to said gingivae lining.

6. The dental device as recited in claim 5 where said chip means includes at least one U-shaped spring element having opposing leg elements secured to said first and second frame walls.

7. The dental device as recited in claim 6 where said first electrode means includes a continuous first electrode strip element secured to said first frame wall.

8. The dental device as recited in claim 7 where said second electrode means includes a continuous second electrode strip element secured to said second frame wall, said second electrode strip element being insulated from said gingivae lining and being in electrical contact with a lip wall of a user.

9. The dental device as recited in claim 3 where said power supply means is encased within a housing formed on one of said first and second walls.

* * * * *